(12) United States Patent
McWhorter

(10) Patent No.: US 8,414,294 B2
(45) Date of Patent: Apr. 9, 2013

(54) DENTAL PROBE WITH BRISTLES

(76) Inventor: Robert D. McWhorter, Pocatello, ID (US)

( * ) Notice: Subject to any disclaimer, the term of this patent is extended or adjusted under 35 U.S.C. 154(b) by 0 days.

(21) Appl. No.: 13/047,391

(22) Filed: Mar. 14, 2011

(65) Prior Publication Data
US 2012/0237888 A1   Sep. 20, 2012

(51) Int. Cl.
*A61C 3/00* (2006.01)
*A61C 17/00* (2006.01)

(52) U.S. Cl. .............. 433/143; 433/141; 433/29

(58) Field of Classification Search .............. 433/29–31, 433/215, 216, 141–148; 132/308–310, 321; 15/167.1, 22.1, 22.2
See application file for complete search history.

(56) References Cited

U.S. PATENT DOCUMENTS

| | | | |
|---|---|---|---|
| 1,852,480 A * | 4/1932 | Ruetz ......................... 132/309 |
| 2,668,973 A | 2/1954 | Glaza et al. |
| 2,765,799 A * | 10/1956 | Ritter ......................... 132/309 |
| 3,935,640 A | 2/1976 | Cohan |
| 4,048,723 A | 9/1977 | Thorup |
| 5,228,166 A | 7/1993 | Gomez |
| 5,323,795 A | 6/1994 | Berens |
| 5,435,033 A * | 7/1995 | Millner ......................... 15/22.1 |
| 5,913,682 A | 6/1999 | Strate |
| 6,041,467 A * | 3/2000 | Roberts et al. ............... 15/167.1 |
| 6,319,004 B1 | 11/2001 | Forsline |
| 6,902,397 B2 * | 6/2005 | Farrell et al. ..................... 433/29 |
| 7,448,107 B2 | 11/2008 | DePuydt |
| 2001/0054211 A1 * | 12/2001 | Cabedo-Deslierres et al. 15/106 |
| 2003/0183242 A1 | 10/2003 | Kemp |
| 2007/0224571 A1 * | 9/2007 | Watson ........................... 433/31 |
| 2009/0035717 A1 * | 2/2009 | Rizoiu et al. ..................... 433/29 |
| 2010/0014909 A1 | 1/2010 | Sampaio |
| 2010/0325822 A1 | 12/2010 | Hilscher |

\* cited by examiner

*Primary Examiner* — Yogesh Patel
(74) *Attorney, Agent, or Firm* — Scott D. Swanson; Dykas & Shaver

(57) ABSTRACT

The present application discloses a method and apparatus for disguising a dental probe from a patient for use, for example, in the field of pediatric dentistry, or special needs dentistry, the apparatus and method of using the apparatus having a first section and a second section. In a preferred embodiment, the first section is a hard probe that is configured for probing a patient's teeth for carious lesions.

6 Claims, 4 Drawing Sheets

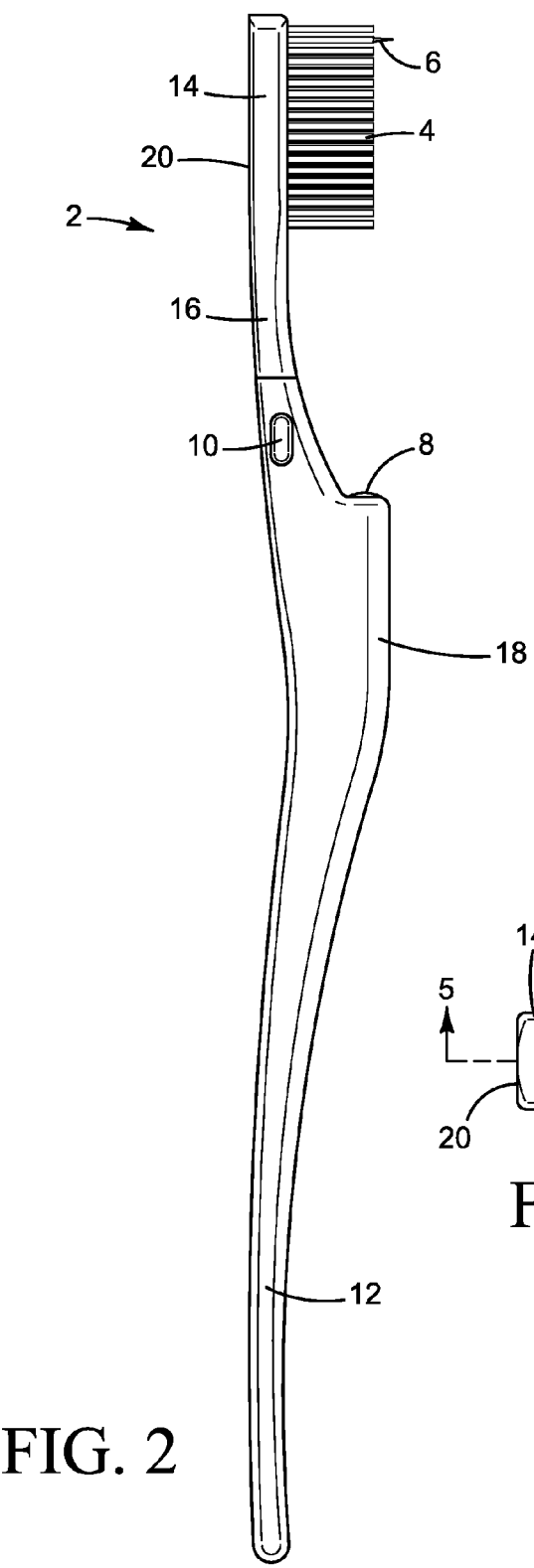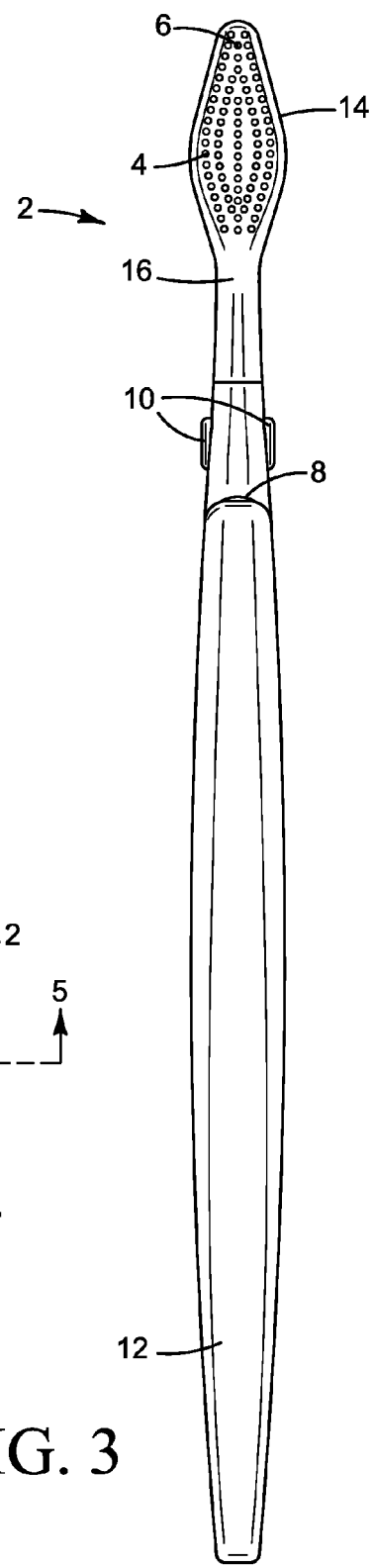
FIG. 2
FIG. 4
FIG. 3

DENTAL PROBE WITH BRISTLES

TECHNICAL FIELD

The presently disclosed and claimed inventive concept(s) generally relate to an apparatus for probing for carious lesions, and more particularly to a disguised probe for probing for carious lesions.

BACKGROUND

The American Dental Association estimates that there are approximately 183,000 active, licensed dentists in the United States. A large number of dentists in the United States use sharp dental explorers to probe for carious lesions. The probes are also used to distinguish between normal and softened dentin, to identify subgingival calculus, and to evaluate the marginal integrity of restorations. The use of a probe, also known as an explorer or sickle probe in the dental field, is well known throughout the dental field and is taught in dental school and practiced by practicing dentists. The explorer is generally used by running the sharp metal probe over a client's teeth. When the explorer catches or resists removal after the insertion into a pit or fissure with moderate to firm pressure and is accompanied by one or more of a softness at the base of the area, opacity adjacent to the pit or fissure, or soft enamel adjacent to the pit or fissure, the dentist typically recognizes a sign of caries. The dental explorer is typically an elongate metal probe that is maintained by sterilization and sharpening. Further the use of a disposable explorer is possible or an explorer with a disposable tip. The explorers can be made of, for example, a hard metal or a hard plastic. Dental explorers are also used to remove plaque from the examination area of a patient's tooth. The plaque is an indication that the area beneath the plaque needs to be examined for the presence of carious lesions. This is typically performed by a scraping action of the explorer shaft or by use of the explorer's tip to expose the underlying enamel surface. The tip of the explorer is also used to determine the presence or absence of surface roughness on the surface of any noncavitated area. In this process the tip of the explorer is moved gently across the surface of the noncavitated area in search of surface roughness that indicates enamel decay.

SUMMARY OF THE DISCLOSURE

The purpose of the Summary is to enable the public, and especially the scientists, engineers, and practitioners in the art who are not familiar with patent or legal terms or phraseology, to determine quickly from a cursory inspection, the nature and essence of the technical disclosure of the application. The Summary is neither intended to define the inventive concept(s) of the application, which is measured by the claims, nor is it intended to be limiting as to the scope of the inventive concept(s) in any way.

The present application discloses a method and apparatus for disguising a dental probe from a patient. This is applicable, for example, in the field of pediatric dentistry, or special needs dentistry. What is disclosed is a dental tool having a first section and a second section. In a preferred embodiment, the first section is a hard probe that is configured for probing a patient's teeth for carious lesions. The second section of the tool has a structure of an object that is familiar to a patient and is used to disguise the presence of the hard probe. For example the second section can be in the shape of a toothbrush, a lollypop, or even a figurine that is familiar to a child. This could be an action figure figurine or similar object. In this way, the dental tool can be used on a child or special needs patient or anyone else and lead to a lower feeling of fear than is experienced with the use of a naked dental explorer. The second section of the dental tool can have a first end and a second end and a length between the first end and the second end. A plurality of bristles is located near the first end and extends outward from the first end. This generally has the shape of the head of a toothbrush. The hard probe is located near the first end in a preferred embodiment. The hard probe can extend outward from the first end either parallel to or in the same direction as the plurality of bristles or in a different direction. Also disclosed is a dental tool in which the hard probe is located within an outer circumference of the plurality of bristles or it can be located on the outer periphery of the plurality of bristles. In a preferred embodiment, the probe is an elongate metal probe. This metal probe can have a rounded section that can be used more efficiently for reaching around a tooth and exploring the back of the tooth. The probe again can be located within the outer perimeter of the bristles, as part of the outer perimeter of bristles, or outside the outer perimeter of bristles.

The dental tool can have a mechanism by which the first end of the dental tool can be removed. This can allow for sterilization or replacement of first end of the dental tool.

The dental tool can have a light in a preferred embodiment for illuminating the working area in which the dental tool is being used. This light can comprise an LED or any other similar light known in the art or discovered in the art. The type of light is not important to the spirit of the invention The dental tool can have a rechargeable energy source that provides power to the light or it can have a replaceable energy source such as a battery to provide power for the light.

Also disclosed is a method for probing for carious lesions in which the method includes providing a device for probing for carious lesions in a mouth. The device has a first section and a second section. The first section of the device is a hard probe and the second section of the device is a section configured to disguise the dental probe such that the dental tool does not appear to include a hard probe. The dental tool subsequently used to probe a tooth for the presence of carious lesions.

In a preferred embodiment, the second section of the dental tool used in the method has a first end and a second end and a length between the first end and the second end. The dental tool has a plurality of bristles located proximate the first end of the dental tool and extending outward from the first end of the dental tool in a generally normal direction to the dental tool. The hard probe, in a preferred embodiment, is located within the outer perimeter of the plurality of bristles, although it can be located outside the outer perimeter or even directly in the outer perimeter of the bristles.

Still other features and advantages of the presently disclosed and claimed inventive concept(s) will become readily apparent to those skilled in this art from the following detailed description describing preferred embodiments of the inventive concept(s), simply by way of illustration of the best mode contemplated by carrying out the inventive concept(s). As will be realized, the inventive concept(s) is capable of modification in various obvious respects all without departing from the inventive concept(s). Accordingly, the drawings and description of the preferred embodiments are to be regarded as illustrative in nature, and not as restrictive in nature.

BRIEF DESCRIPTION OF THE DRAWINGS

FIG. 2 is a side view of an embodiment of the invention.

FIG. 3 is a front view on an embodiment of the invention.

FIG. 4 is a top view of the invention with cross-sectional line 5 illustrated.

DETAILED DESCRIPTION OF THE EXEMPLARY EMBODIMENTS

Figure 1:
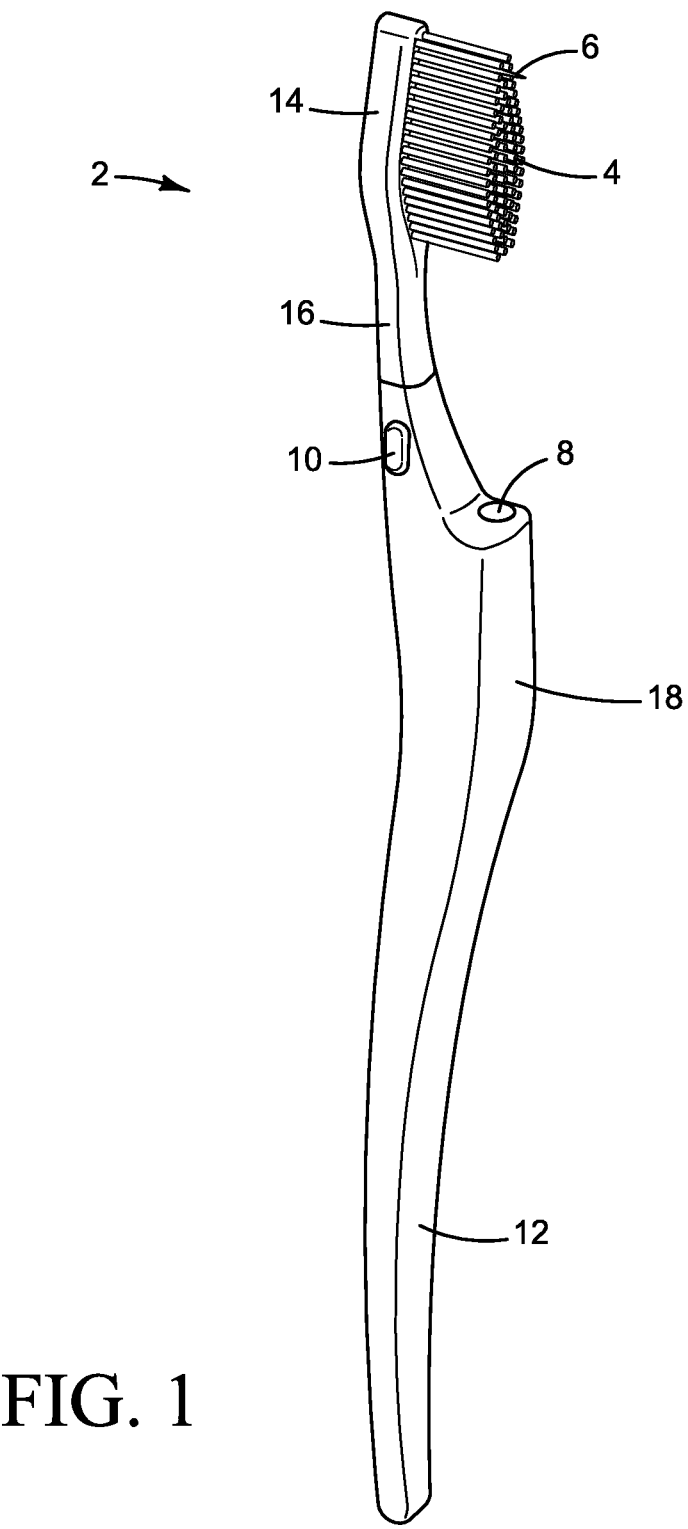
FIG. 1 is a perspective view of an embodiment of the invention.

While the presently disclosed inventive concept(s) is susceptible of various modifications and alternative constructions, certain illustrated embodiments thereof have been shown in the drawings and will be described below in detail. It should be understood, however, that there is no intention to limit the inventive concept(s) to the specific form disclosed, but, on the contrary, the presently disclosed and claimed inventive concept(s) is to cover all modifications, alternative constructions, and equivalents falling within the spirit and scope of the inventive concept(s) as defined in the claims.

The use of "e.g.," "etc," and "or" indicates, throughout this document, non-exclusive alternatives without limitation unless otherwise noted.

The use of "including" means, throughout this document, "including, but not limited to," unless otherwise noted.

FIG. 1 illustrates a preferred embodiment of the invention of the present application. FIG. 1 illustrates an embodiment of the invention as a dental tool that has a toothbrush section 4 disguising a probe 6. In a preferred embodiment the probe is a hard metal probe within a series of bristles. The bristles are located on the head, or first end of the dental tool 14. The dental tool has a mechanism 10 for attaching a removable head 16 that is present in a preferred embodiment of the invention. This mechanism can comprise a variety of connection mechanisms including, for example, a detent mechanism, a clip in mechanism, or a snap lock connection. In a further preferred embodiment, the dental tool has a light 8 for illuminating the area in which a user of the dental tool is working on. The light and associated battery in the depicted embodiment are contained in the handle of the dental tool 12, although a variety of assemblies can be used without detracting from the spirit of the invention.

FIG. 2 illustrates a side view of the embodiment of the invention. As depicted, the probe 6 in the depicted embodiment extends past the end of the bristles 4, protruding away from the first section of the dental tool 14.

FIG. 3 illustrates a front view of an embodiment of the invention. As depicted the invention has the probe 6 within an exterior periphery of the plurality of bristles. While depicted is a straight probe, the probe can come in a wide variety of shapes and sizes. These include curved and/or straight probes.

The probe of a preferred embodiment and as depicted ends in a point that is used to search for weakening in the enamel of the tooth. While in a preferred embodiment a dental tool is depicted, a wide variety of mechanisms can be used to conceal the probe from a patient. In a preferred embodiment, the light source is an LED, however a wide variety of light sources can be used including standard light bulbs, LED, and any other variety of light that is currently known or developed in the future.

Figure 5:
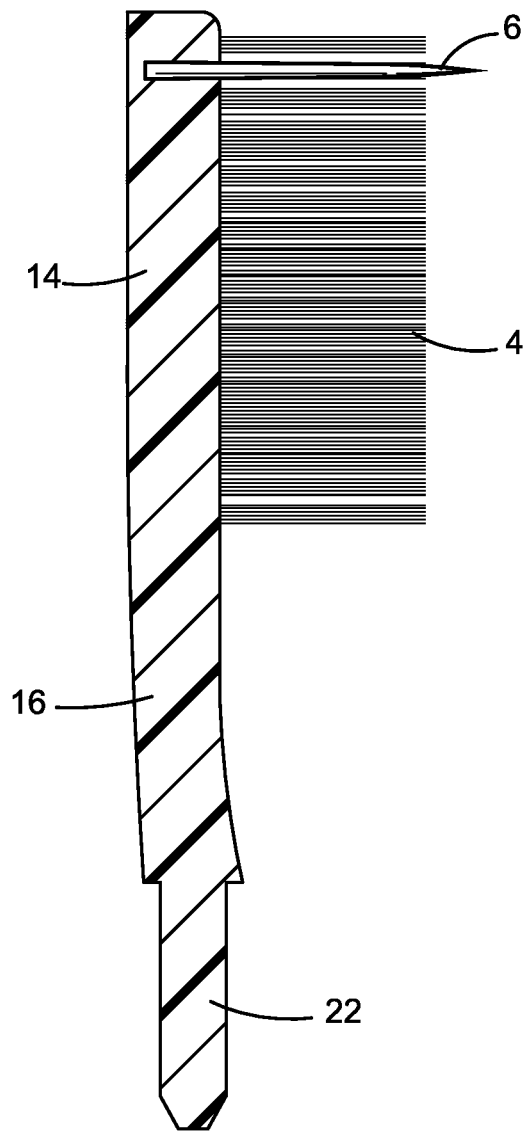
FIG. 5 is a cross-section of line 5 found in FIG. 4.
Figure 7:
FIG. 7 is a view of a section of an embodiment of the invention.

FIG. 4 depicts a view from above of the dental tool and probe 6. In this embodiment the probe 6 appears to be on the outer periphery of the dental tool bristles. FIG. 5 illustrates that the probe 6 is embedded within the first section of the dental tool 14. Also shown is a male connector portion 22 of a removable head 16 of the dental tool. The male end fits into the female 30 of FIG. 7. FIG. 7 depicts the handle of the dental tool appearing object without the removable head attached. The opening 32 can serve as an input jack for power for charging the battery of the light.

Figure 6:
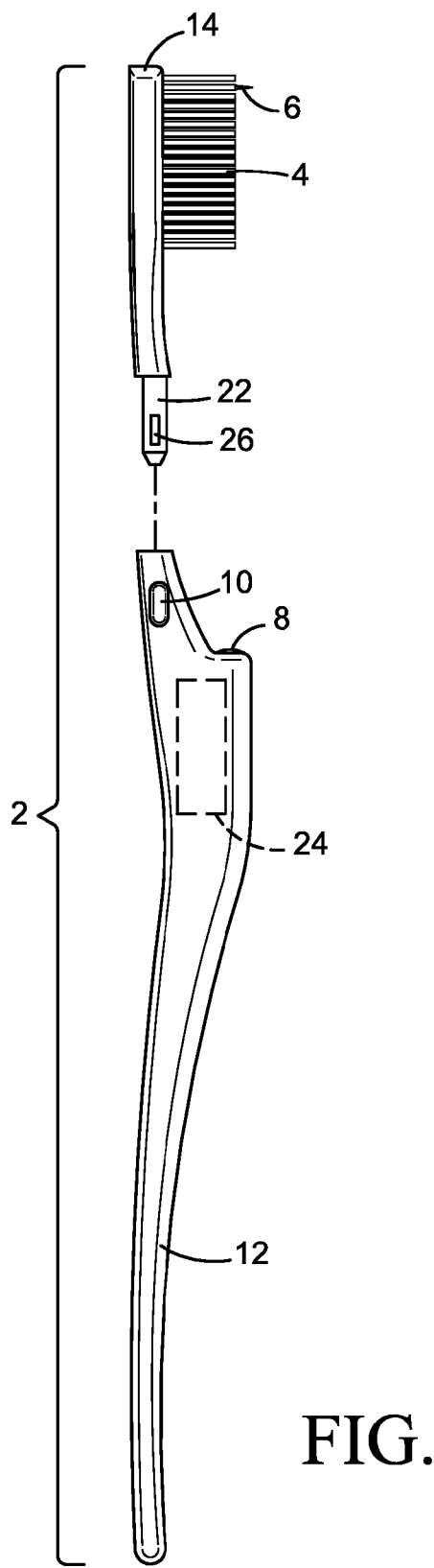
FIG. 6 is an exploded view of a preferred embodiment of the invention.

FIG. 6 illustrates the removable head of the dental tool and the mechanism by which it attaches to the handle of the dental tool. The removable head has a resilient pin 26 that extends into the opening 10 in order to hold the removable head onto the dental tool handle. FIG. 6 illustrates the location of a potential battery 24 or similarly an untracapacitor or other power storage unit could be used in the dental tool.

What is claimed is:

1. A dental tool for probing for carious lesions comprising:
    a first end portion and a second end portion and a length between said first end portion and said second end portion;
    a plurality of tooth-brushing bristles located at said first end portion of said dental tool and extending in a first normal direction from said first end portion of said dental tool, wherein said bristles defining an outer perimeter; and
    a hard probe non-movably secured in said first end portion of said dental tool and extending outward from said first end portion of said dental tool in a normal direction, wherein said hard probe comprises an elongate metal probe, wherein said hard probe is secured in said first end portion of said dental tool interior to said outer perimeter defined by said plurality of bristles.

2. The dental tool of claim 1, wherein said probe comprises a rounded section.

3. The dental tool of claim 1, wherein said dental tool comprises a mechanism for removing said first end portion of said dental tool.

4. The dental tool of claim 1, wherein said dental tool comprises a light source configured to illuminate an area of a patient's mouth.

5. The dental tool of claim 4, wherein said dental tool comprises a rechargeable energy source configured for providing power to said light source.

6. The dental tool of claim 1, wherein said probe having a height which is greater than a height of said bristles.

* * * * *